United States Patent [19]
Shaw

[11] Patent Number: 5,623,106
[45] Date of Patent: Apr. 22, 1997

[54] METHOD AND APPARATUS FOR FORMING DISPOSABLE TIPS IN AN ANALYZER

[75] Inventor: James D. Shaw, Hilton, N.Y.

[73] Assignee: Johnson & Johnson Clinical Diagnostics, Inc., Rochester, N.Y.

[21] Appl. No.: 471,995

[22] Filed: Jun. 6, 1995

[51] Int. Cl.[6] .................................................. G01N 35/10
[52] U.S. Cl. ........................................................ 73/864.14
[58] Field of Search ........................... 73/864.14, 864.21, 73/864.23–864.25; 422/100, 104; 436/180; 83/198

[56] References Cited

U.S. PATENT DOCUMENTS

| | | | |
|---|---|---|---|
| 3,405,577 | 10/1968 | Cousino | 83/198 |
| 3,469,750 | 9/1969 | Vanderbeck | 83/198 |
| 3,484,206 | 12/1969 | Loebl | 23/253 |
| 3,736,099 | 5/1973 | Begg et al. | 23/259 |
| 4,212,204 | 7/1980 | St. Amand | 73/425.6 |
| 4,261,205 | 4/1981 | Oshikubo et al. | 422/100 |
| 4,347,875 | 9/1982 | Columbus | 141/18 |
| 5,133,218 | 7/1992 | Uffenhiemer et al. | 73/864.14 |
| 5,453,246 | 9/1995 | Nakayama et al. | 73/864.25 |

FOREIGN PATENT DOCUMENTS

0182943A1  11/1984  European Pat. Off. .......... B01L 3/02

*Primary Examiner*—Robert Raevis
*Attorney, Agent, or Firm*—Dana M. Schmidt

[57] ABSTRACT

A method and apparatus for forming in situ a new disposable tip for a dispensing probe within an analyzer, by feeding a continuous stock of tube through two die plates and severing the tube by relative motion of the die plates, while holding the cut portion in the dispensing probe temporarily inserted into one of the die plates. The tip is ejected from the probe in a direction opposite to the direction of insertion of the tube into the die plates and dispensing probe.

9 Claims, 7 Drawing Sheets

METHOD AND APPARATUS FOR FORMING DISPOSABLE TIPS IN AN ANALYZER

FIELD OF THE INVENTION

This invention is directed to a method and apparatus for making disposable tips for a dispensing probe of an analyzer, preferably within and as part of the analyzer.

BACKGROUND OF THE INVENTION

It is the general practice in many analyzers to use disposable tips on permanent dispensing probes, so that each new sample is aspirated into, and dispensed out of, a new tip. Hence, cross-contamination between samples is avoided.

It is also customary to provide such tips premade with specific, fairly complex shapes, as shown for example as the "rocket" shape in U.S. Pat. No. 4,347,875, to provide for certain dispensing functions. Although such tips work admirably, they have a few drawbacks: they are somewhat expensive to mold, and because they are supplied as discrete parts, they are not easily and quickly added to the analyzer and mated with the dispensing probe. Delays in the later are not significant, except if a high-speed analyzer is desired with maximum throughput.

On the other hand, it is old in the art to provide a very inexpensive pipette which comprises only a continuous cylindrical plastic tubing, of considerable length, and to compress a significant part of the length between two plates to a) aspirate, and then b) dispense liquid sucked into the portion not compressed. When dispensing is complete, the tubing is simply advanced by counter-rotating rollers until a knife can cut off the used portion, and a new portion of the continuous tubing is then presented for use. Examples are disclosed in U.S. Pat. No. 3,736,099. Although such an approach solves the problem of expense, it relies on exterior plates to compress the tube to generate aspiration and dispensing pressure. Such a mechanism is not as accurate as the pumps that have been conventionally used with the permanent probes that mount the tips described in the '875 patent. That is, the collapsing of the tubing to generate pressures, can be variable. Also, this approach is limited to the use of resiliant tubes and thus excludes the use of rigid tubes. Accurate dispensing has become very important, in this age of quantitative assays conducted using, e.g., dried slide test elements, given that very small total volumes of liquid are used (10 μL). An error of 5 μL, though not large when pin-pricking a linger for home-testing of blood, makes a 50% difference if the total optimum volume is 10 μL.

Hence, the continuous tubing approach has never achieved a significant commercial status as a disposable pipette tip, notwithstanding its availability in the public literature since 1973.

Thus there has been a need for a method and apparatus for making a disposable tip, that is as inexpensive as a continuous cylindrical tubing, but which has the accuracy of the more expensively molded "rocket" tips.

SUMMARY OF THE INVENTION

I have devised apparatus and a method of making tips that allows the continuous tubing to be used for the tips without sacrificing dispensing accuracy.

More specifically, there is provided, in accord with a first aspect of the invention, a method of making a pipette tip for mounting inside a port of a pipette of a dispensing probe, comprising the steps of:

a) pushing cylindrical stock of continuous length through first and second die plates having first surfaces facing and in sliding contact with each other, and first and second apertures respectively therein and generally aligned with each other to form an axis through which the cylindrical stock passes, the second of the plates having a third aperture that is generally coaxial with the second aperture of the second plate and extending from a surface of second plate opposite to the first surface;

b) inserting a receiving port of a pipette or dispensing probe into the third aperture;

c) pushing the stock far enough through the first and second die plates until the stock is frictionally engaged within the port of a pipette or dispensing probe in the third aperture; and d) sliding the facing plates relative to each other in a direction generally traverse to the axis until the sliding acts to sever the stock to create a tip for the port in the second aperture.

In accord with a second aspect of the invention, there is provided a method of repeated creation and use of disposable tips at a dispensing station of an analyzer comprising a probe for aspirating and dispensing liquid into and out of tips. The method comprises the steps of a) engaging a port of the probe with a continuous tube by moving the tube to the port in a first direction;

b) cutting off a portion of the tube so as to leave some of the tube projecting from the probe port, c) using the cut off tube portion as the disposable tip for aspirating and dispensing a first liquid sample, d) ejecting the cut-off tube in a direction opposite to the first direction, e) moving the continuous tube along the first direction back to the probe port until it reengages the probe, and f) repeating the steps b) and c) with a second liquid sample.

In accord with a third aspect of the invention, there is provided apparatus for forming a pipette tip inserted into a port of a pipette or a dispensing probe, the apparatus comprising first and second die plates having first surfaces facing and in sliding contact with each other, and first and second apertures respectively therein, generally aligned with each other to form an axis, the second of the plates having a third aperture generally coaxial with the first aperture of the second plate, for receiving a port of the pipette or dispersing probe therein, means for sliding the plates relative to each other along the first surfaces in a direction generally transverse to the axis, and engaging means for frictionally engaging and forcing a continuous cylindrical stock through the plates to create a pipette tip.

In accord with a fourth aspect of the invention, there is provided a dispensing station in an analyzer for assaying analytes in a biological liquid, the station comprising:

a probe having a port for mounting a disposable tip;

pressurizing means for generating plus and minus pressures relative to ambient, within the port;

first and second die plates having first surfaces facing and in sliding contact with each other, and first and second apertures respectively therein, generally aligned with each other to form an axis, the second of the plates having a third aperture generally coaxial with the first aperture of the second plate, for receiving a port of the probe therein;

means for sliding the plates relative to each other along the first surfaces in a direction generally transverse to the axis; and engaging means for frictionally engaging and forcing a continuous cylindrical stock through the plates to create a pipette tip.

Accordingly, it is an advantageous feature of the invention that a disposable tip can be manufactured out of a simple cylindrical tube without sacrificing dispensing accuracy.

It is a related advantageous feature of such a tip that it can be manufactured and assembled automatically by the analyzer, as needed, avoiding the need for manual loading of individual tips.

Other advantageous features will become apparent upon reference to the Detailed Description that follows, when read in light of the attached drawings

DESCRIPTION OF THE PREFERRED EMBODIMENTS

The invention is described hereinafter in connection with preferred embodiments, wherein preferred dies are used to sever individual tips from continuous stock of cylindrical shape, fed by counter-rotating rollers, to dispense sample liquid. In addition, the invention is useful regardless of the severing mechanism used, or the shape of the continuous stock, or whether the advancing means used are rollers or some other device. Additionally, it is useful regardless of the type of liquid being aspirated and dispensed, and regardless of the type of test material receiving the liquid.

Figure 1:
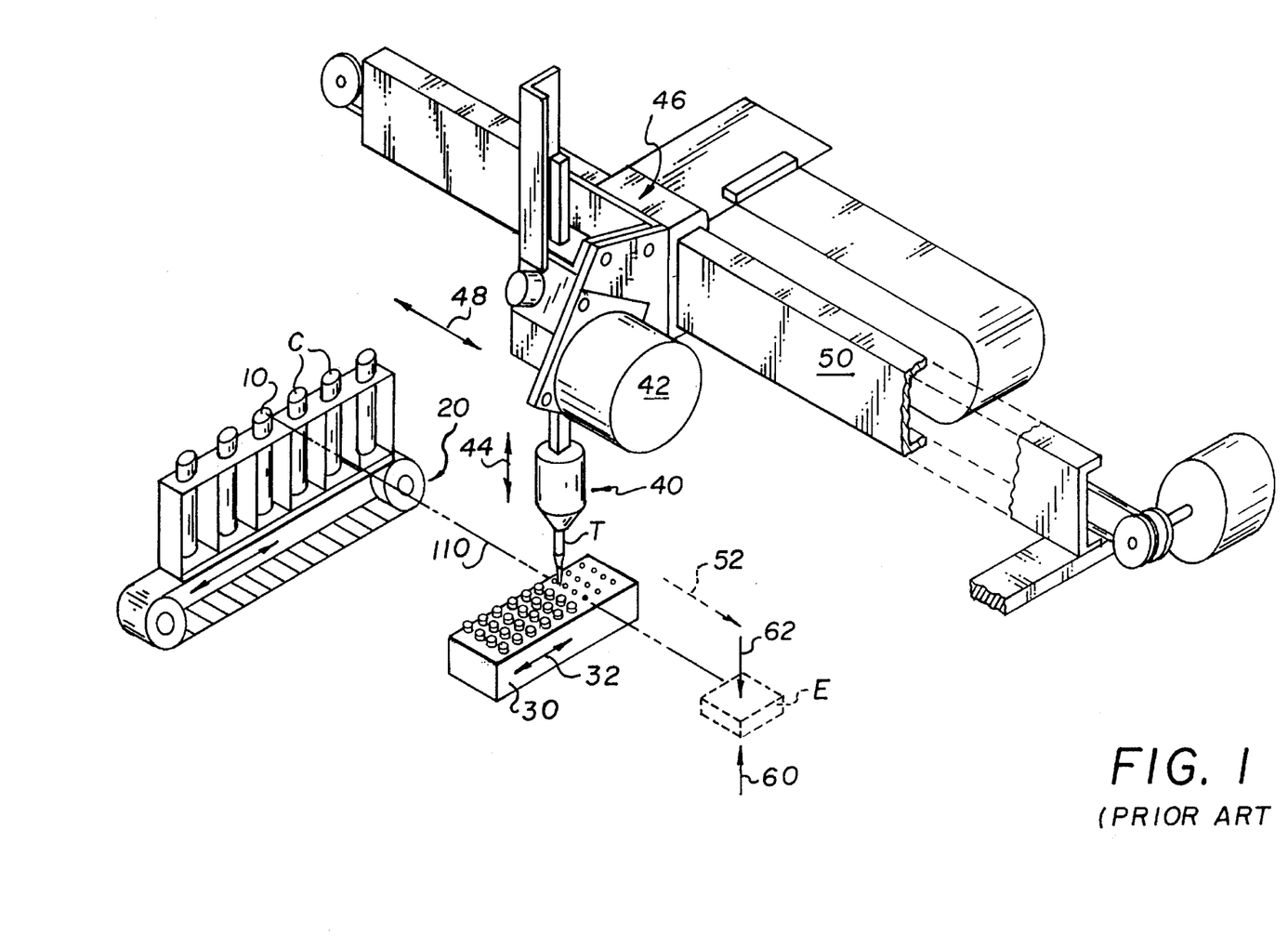
FIG. 1 is an isometric view of the sample handling portion of a conventional analyzer, demonstrating tip-loading and the dispensing station.

The problem solved, and the environment of, the invention are illustrated in FIG. 1, which shows particular prior art, e.g., the analyzer of U.S. Pat. No. No. 5,008,082. In such a conventional analyzer, patient sample liquid is supplied by containers C (shown as tubes) carried by a carrier 10 which is shown to be linear and linearly driven by a belt 20. Alternatively, carrier 10 can be a rotor that is rotated. Disposable tips T are provided pre-made, e.g., as the "rocket" type of U.S. Pat. No. 4,347,875, and are supplied on a tray 30 that advances linearly, arrow 32, but which can alternatively also be a rotor. A dispensing probe 40 is connected to a pump 42 for creating aspirating vacuum and dispensing pressure, as is well-known. Probe 40 in turn is mounted for vertical reciprocation, arrow 44, on a carrier 46 that traverses linearly, arrow 48, along a track 50. The purpose, of course, is to cause probe to move first to tray 30 to pick up a tip T, then to carrier 10 to aspirate a liquid sample into the tip from a container C, and then back, arrow 52, to a new station 60 which is the dispense station where tip T is lowered, arrow 62, to allow liquid sample to be dispensed onto a dried slide test element E, such as those available from Clinical Diagnostic Systems, Inc., a Johnson & Johnson company, under the trademark "Ektachem".

Such has been the state-of-the-art for disposable tip usage in analyzers, primarily. The only drawback has been that tray 30 requires manual loading of the tips, by an operator or operator assistant, and hence pre-manufacture of the tips, and in a special mold.

Figure 2:
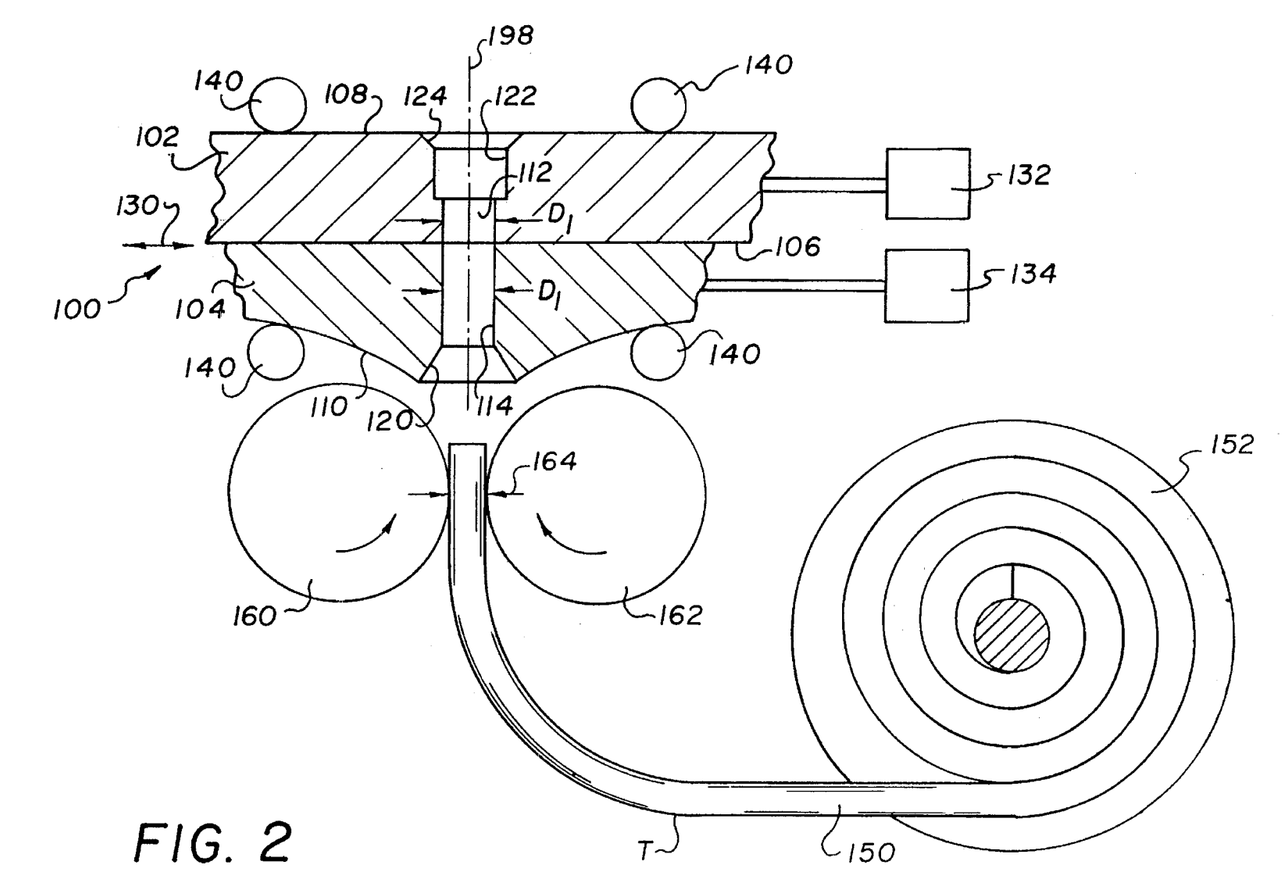
FIG. 2 is a fragmentary elevational view, partly in section, of the tip creating apparatus of the invention.

In accordance with the invention, FIG. 2, tray 30 and the premanufacture of the tips are replaced by a mechanism 100, FIG. 2, which is part of the automated analyzer. This mechanism comprises first and second opposing die plates 102, 104 each having a sliding contact surface 106 that contacts the other plate and a surface 108, 110, respectively, opposite to surface 106. Each surface 106 in turn is apertured at 112, 114, respectively, with preferably a cylindrical shape of substantially matching diameters D1. Opposing surface 110 is either the exit location of aperture 114, or optionally it can be chamfered, as shown at 120. Opposing surface 108 is preferably provided with yet another aperture 122 that is cylindrical and coaxially aligned with aperture 112, albeit with a diameter larger than D1. Because its function is to receive the port end of a dispensing probe (shown hereinafter), it optionally can also be chamfered at 124.

To provide for relative sliding motion of plate 102 with respect to plate 104, arrows 130, either or both of the plates is connected to a driver 132,134 respectively. Such drivers comprise any conventional mechanism, such as a rack-and-pinion drive using a stepper motor, a hydraulic piston drive, or a belt drive. Constraining rollers or equivalent mechanisms 140, such as tracks, are used to keep plates 102 and 104 from moving out of their position planes shown in FIG. 2.

The actual disposable tip is formed from a continuous stock of a hollow tube T having preferably a substantially cylindrical cross-sectional shape of constant diameter, selected from any suitable plastic, e.g., those used conventionally for tip manufacture. This tube is supplied from an "endless" supply, such as large roll 150 (having side flanges on both sides to confine the roll, only flange 152 being shown.)

To engage and advance tube stock T, means such as opposite and counter-rotating rollers 160,162 are provided, having a nip 164 spaced to frictionally engage tube T. Nip 164 is coaxially aligned with aperture 114 at least during the tube stock-advancing stage. Rollers 160,162 are driven by any suitable, conventional mechanism.

Alternative tube-advancing means include oscillating jaws, not shown, that clamp on the tube, advance it into the die plates, unclamp, and return to the first position for clamping.

Figure 3:
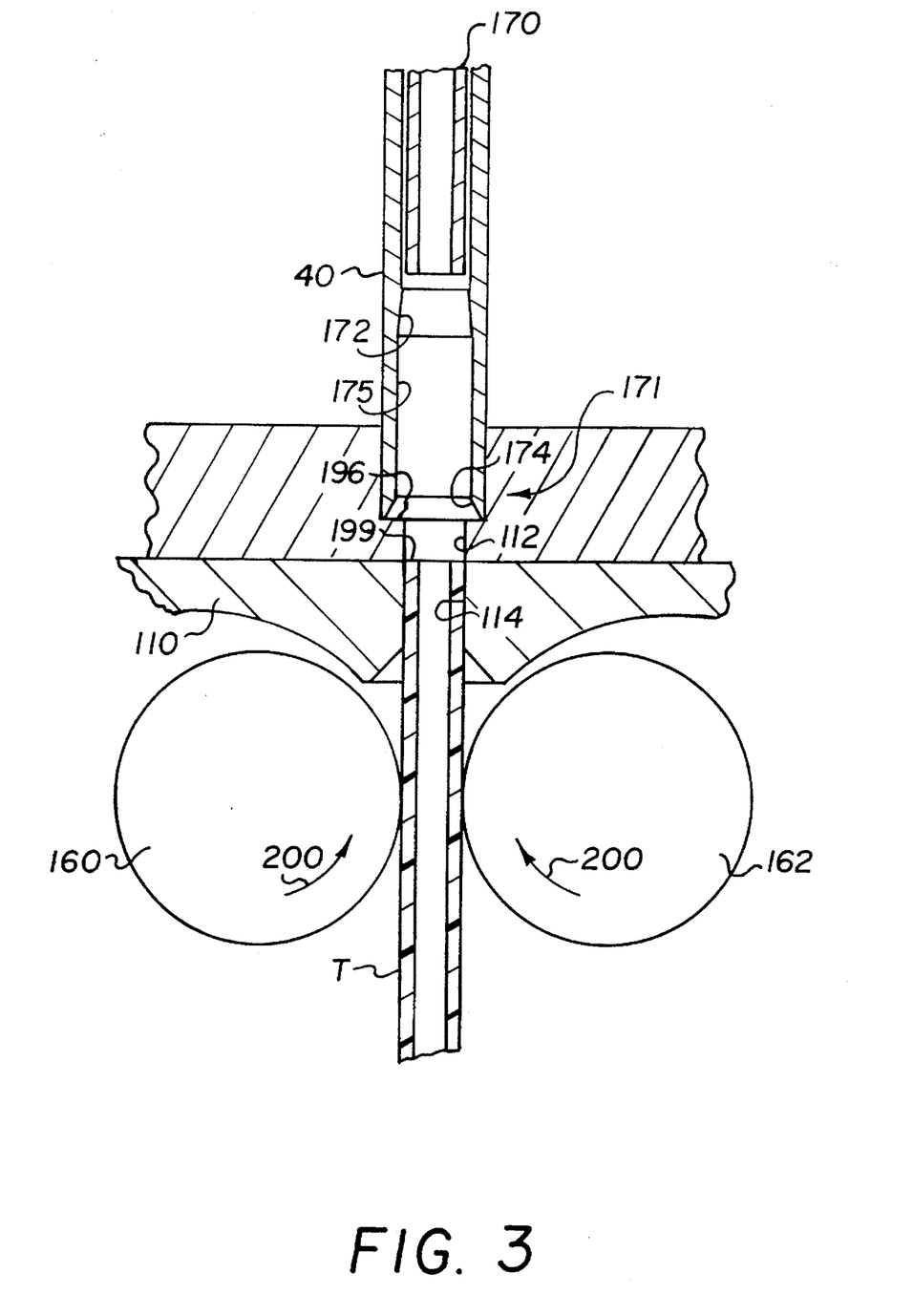
FIG. 3 is a view similar to that of FIG. 2, but illustrating an aspirating probe in place for the initiation of tip creation in accordance with the invention.

The dispensing probe 40 is also preferably further modified, FIG. 3, to include a hollow ejector cylinder 170, mounted inside port 171 of probe 40, because the preferred embodiment provides for the tip to be engaged inside the probe, rather than outside. Alternatively if the tip formed from tube T, as described hereinafter, is inserted over and around the outside of the probe, as is the case with tips T of the aforesaid '082 patent, then the ejector can be mounted on the outside of probe 40.

Probe 40 is further preferably modified to include a chamfered surface 172 of gradually reduced or tapered diameter, spaced away from extreme end 174 of the probe. This leaves a hollow bore 175, of slightly larger diameter than that of 172. The taper of surface 172 is such as to squeeze onto the extreme end 199 of tube stock T as it is fed into the probe, thus positively engaging what becomes the "tip".

Figure 4:
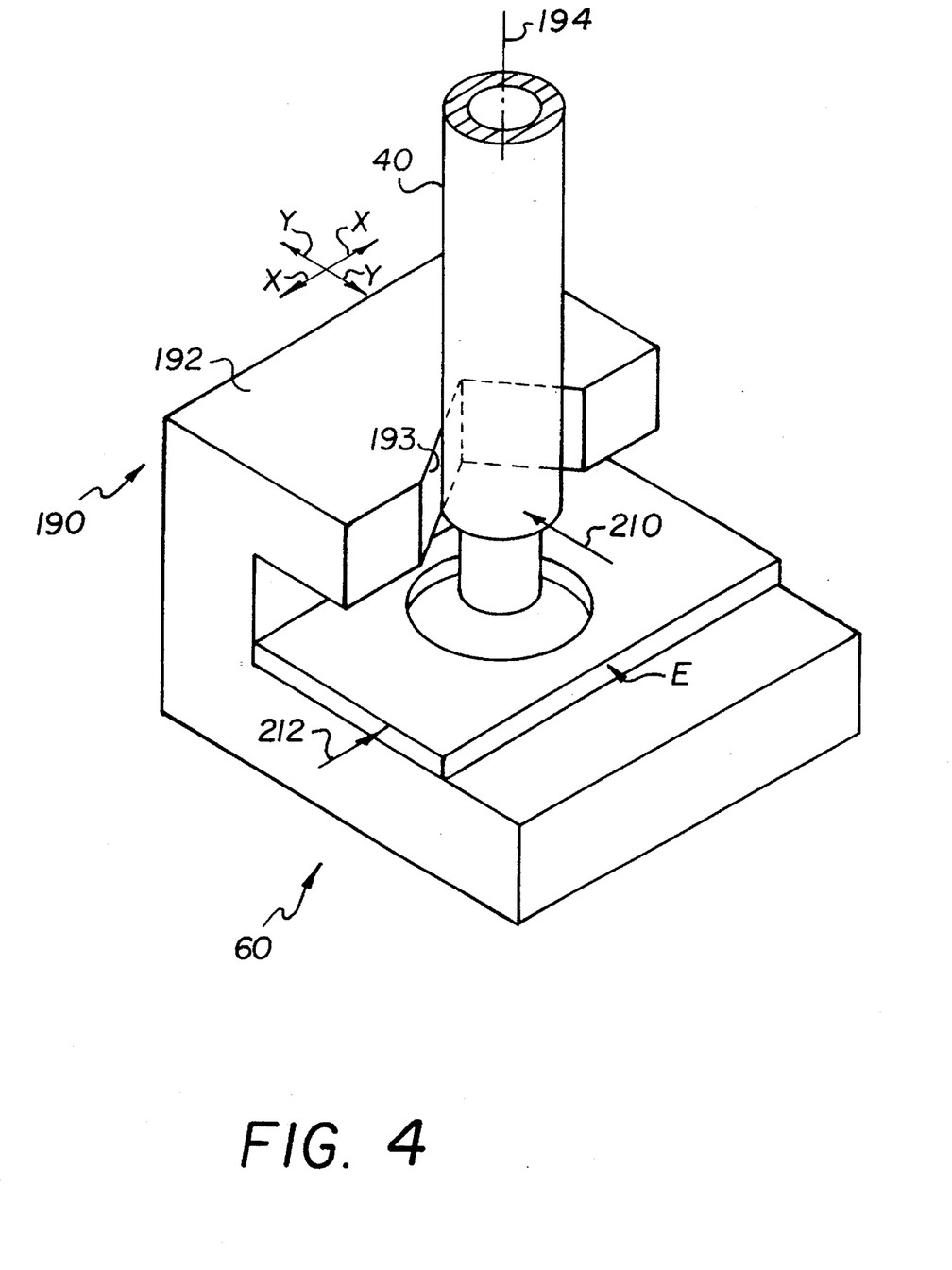
FIG. 4 is a fragmentary isometric view of apparatus used at the dispensing station in conjunction with the rest of the invention.

Yet another structural modification is to optionally include at dispensing station 60, as is more clearly shown in FIG. 4, a sideways support 190 comprising a plate 192 having a v-shaped notch 193 with a vertical axis 194, to receive a formed tip and to stabilize it during dispensing, as discussed below.

METHOD OF OPERATION

This will have become apparent from the aforesaid description. In detail, as shown in FIGS. 3 and 5–9, it proceeds as follows:

Probe 40 is inserted into aperture 122, FIG. 3, and seated on a shoulder 196 that is the junction between aperture 112 and aperture 122. To engage port 171 with tube T, plates 102 and 104 are slidably adjusted so that apertures 114 and 112 are aligned coaxially along a stock-passage axis 198, FIG. 2. Then FIG. 3, the extreme end 199 of tube T is moved into, first, aperture 114 by pushing it through the rotation of rollers 160, 162, arrows 200. The rollers continue to push tube T in direction A through aperture 112, FIG. 5, into port 171 until end 199 of tube T seats frictionally within chamfer 172.

Figure 6:
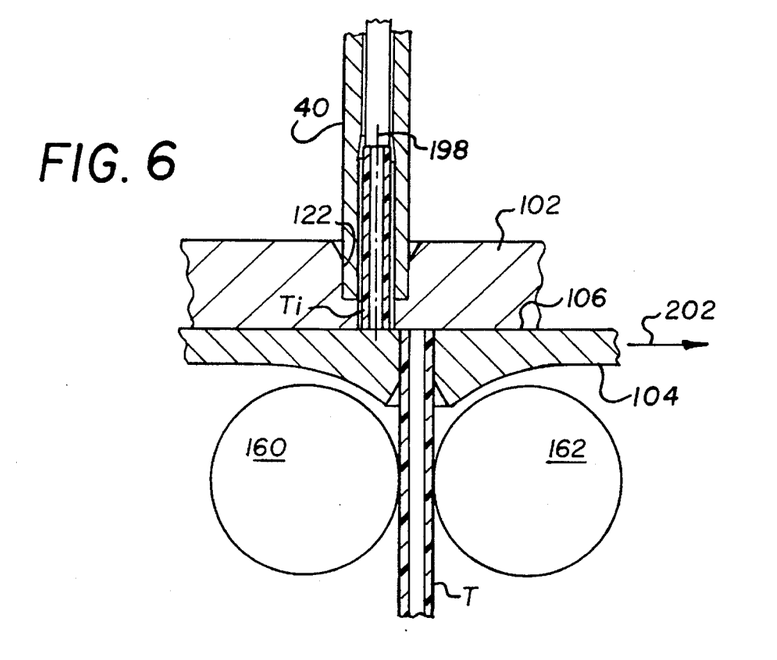
Figure 7:
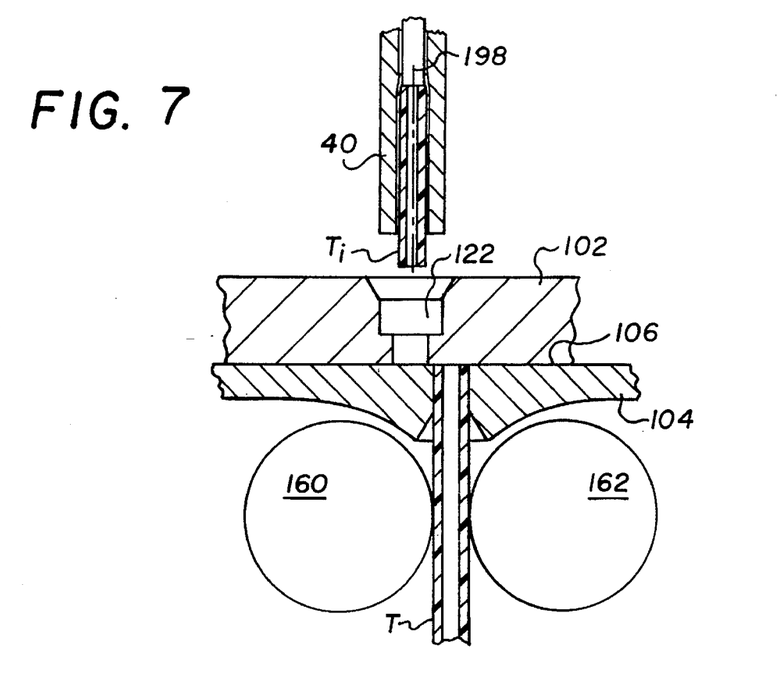
Figure 8:
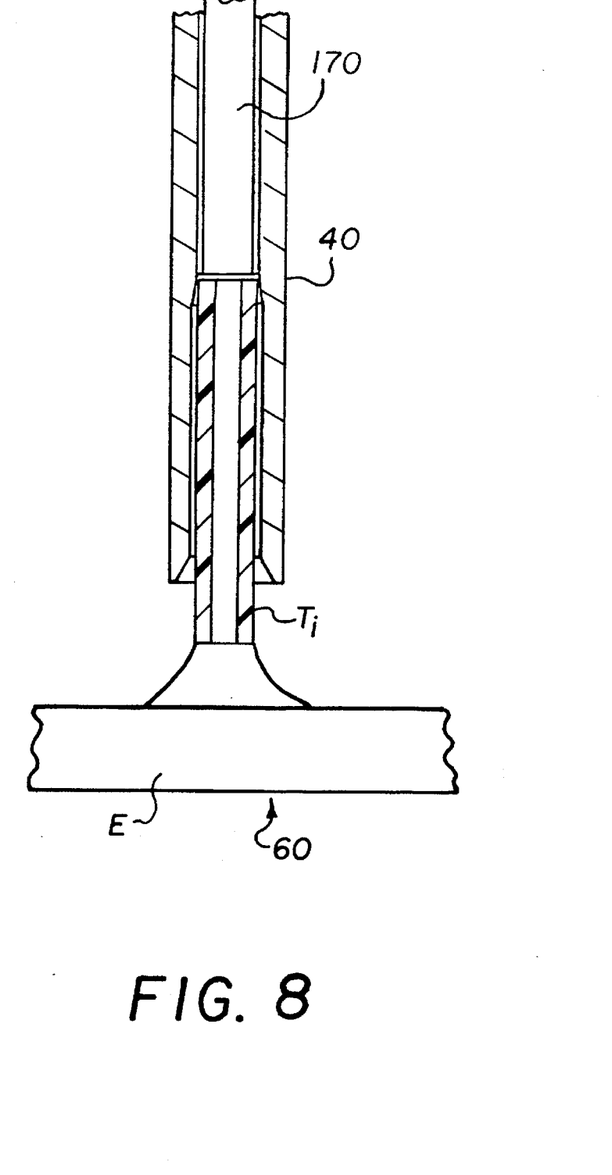

To cut off a portion of tube T to create the actual disposable tip $T_i$, FIG. 6, the two plates are slid sideways relative to each other in a direction 202 generally traverse to axis 198, in this case by moving just plate 104. This severs tube $T_i$ at the contacting faces 106 of the die plates. Probe 40 is then withdrawn from aperture 122, FIG. 7, along with tip $T_i$, and is moved to a sample container, such as a container C, FIG. 1, where tip $T_i$ only, is inserted into the liquid to aspirate it. Then probe 40, tip $T_i$, and its liquid are moved to a dispensing station, such as station 60, FIG. 1, to dispense a portion or all of the aspirated liquid, FIG. 8, onto a slide test element E. It is at station 60, FIG. 4, that plate 192 and notch 193 press against probe 40 as that tip is moved into place for liquid dispensing, arrow 210. Slide test element E is preferably advanced into and out of station 60 in direction 212. Notch 193 then acts to hold probe 40 and tip $T_i$ restrained against undesirable x,y directional movement.

Figure 5:
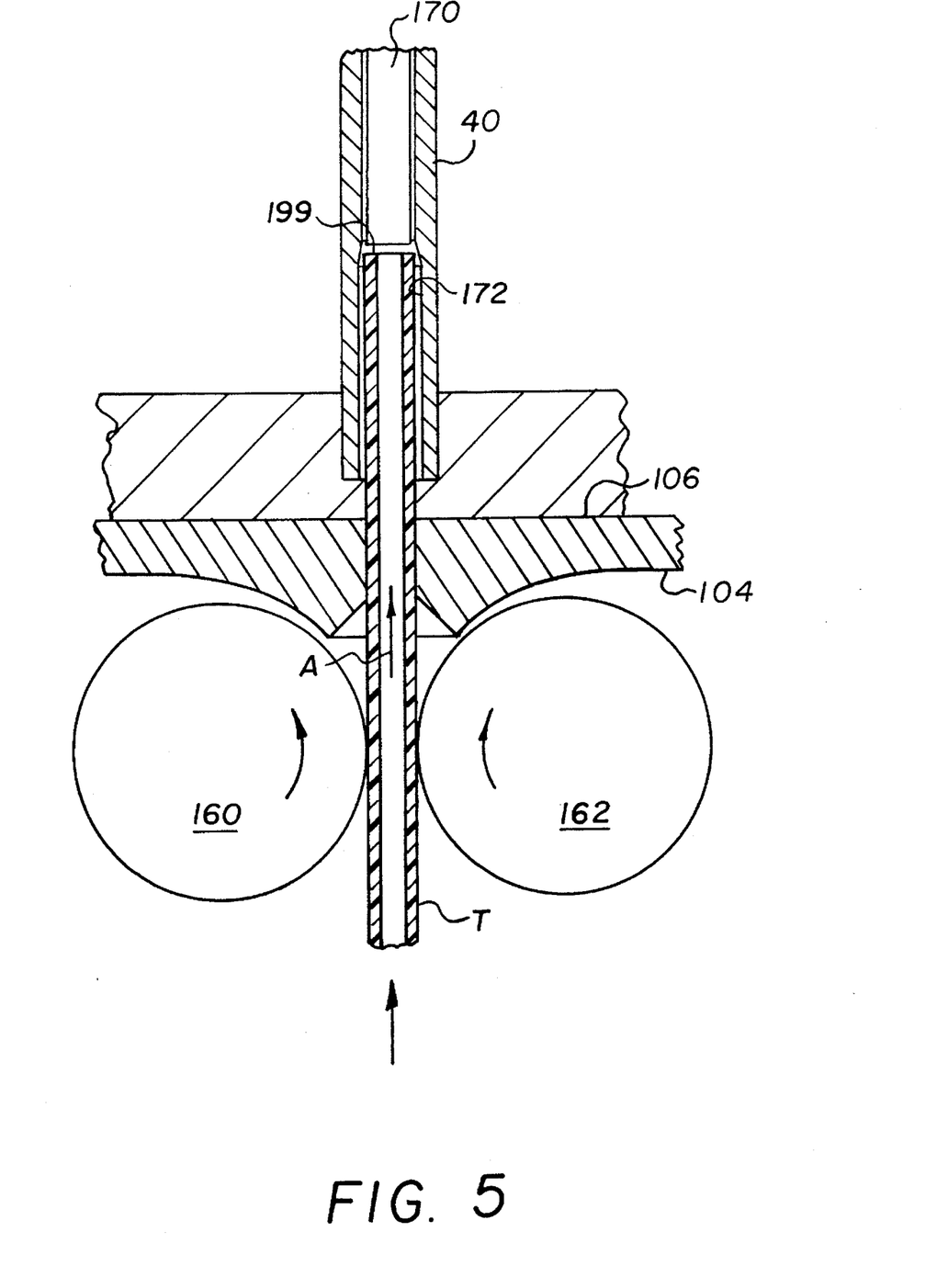
FIGS. 5–9 are views similar to that of FIG. 3 but illustrating subsequent steps in the use of the invention.
Figure 9:
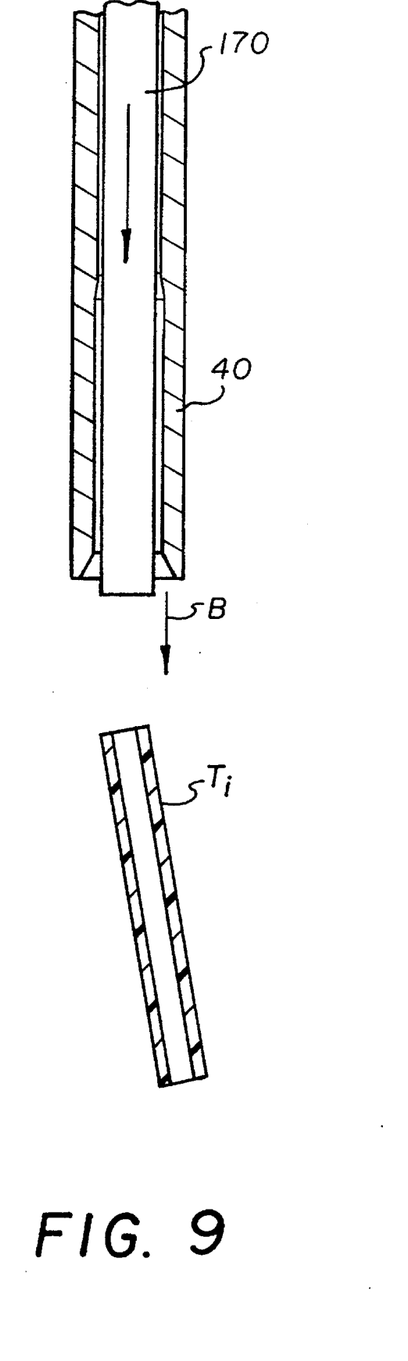

When that sample liquid is finished, ejector 170 advances through probe 40, FIG. 9, to force tip $T_i$ out of its engagement within probe 40, in direction B opposite to direction A, FIG. 5.

Probe 40 is then returned to its position wherein it is inserted into and seated within aperture 122, so that it can receive once again, tube T along direction A, FIG. 5, with a new extreme end for engagement within chamfered surface 172. The tube cutting process, and tip usage, is repeated to create a new disposable tip $T_{i+1}$ (not shown) for use with the next sample liquid. The process is used repeatedly, to create up to $T_{i+n}$ new tips.

ALTERNATE EMBODIMENTS

In addition to those described above, tube T can be selected from conductive plastics, instead of non-conductive plastics. That is, it can comprise a polymer having sufficient carbon black particles as to render tip $T_i$, $T_{i+1}$ and $T_{i+n}$ electrically conductive. As a result, probe 40 can sense the liquid level in containers C, using tip $T_i$, $T_{i+1}$ or $T_{i+n}$ and a capacitance sensing circuit to detect when the tip contacts the liquid, as is well-known. See, e.g., U.S. Pat. No. 4,326,851.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A method of making a pipette tip for mounting inside a port of a pipette of a dispensing probe, comprising the steps of:

a) pushing cylindrical stock of continuous length through first and second die plates having first surfaces facing and in sliding contact with each other, and first and second apertures respectively therein and generally aligned with each other to form an axis through which said cylindrical stock passes, the second of said plates having a third aperture that is generally coaxial with said second aperture of said second plate and extending from a surface of second plate opposite to said first surface, b) inserting a receiving port of a pipette or dispensing probe into said third aperture, c) pushing said stock far enough through said first and second die plates until said stock is frictionally engaged within the port of a pipette or dispensing probe in said third aperture, and d) sliding said facing plates relative to each other in a direction generally traverse to said axis until said sliding acts to sever said stock to create a tip for said port in said second aperture.

2. A method as defined in claim 1, and further comprising the step of removing said pipette or probe with said tip, by withdrawing them out of said second aperture, and thereafter inserting an empty port of a pipette or dispensing probe into said second aperture, realigning said first and second apertures of said plates, and pushing said continuous stock through said plates until said stock is frictionally engaged in said empty port to allow creation of a new tip.

3. A method as defined in claims 1 or 2, wherein said pushing step comprises engaging said cylindrical stock with a pair of opposed rollers having a nip sized to frictionally engage said stock, and counter-rotating said rollers.

4. A method as defined in claims 1 or 2, wherein said port is a port of a dispensing probe that is part of a dispensing mechanism of an analyzer for analytes of biological liquids, and wherein said method of making is repeated each time and before a new sample of the liquids is to be aspirated by said dispensing probe.

5. Apparatus for forming a pipette tip inserted into a port of a pipette or a dispensing probe, the apparatus comprising first and second die plates having first surfaces facing and in sliding contact with each other, and first and second apertures respectively therein, generally aligned with each other to form an axis, the second of said plates having a third aperture generally coaxial with said first aperture of said second plate, for receiving a port of said pipette or dispersing probe therein, means for sliding said plates relative to each other along said first surfaces in a direction generally transverse to said axis, and engaging means for frictionally engaging and forcing a continuous cylindrical stock through said plates to create a pipette tip.

6. Apparatus as defined in claim 5, wherein said engaging means comprise a pair of opposite, oppositely-rotating rollers.

7. A dispensing station in an analyzer for assaying analytes in a biological liquid, said station comprising a probe having a port for mounting a disposable tip, pressurizing means for generating plus and minus pressures relative to ambient, within said port;

first and second die plates having first surfaces facing and in sliding contact with each other, and first and second apertures respectively therein, generally aligned with each other to form an axis, the second of said plates having a third aperture generally coaxial with said first aperture of said second plate, for receiving a port of said probe therein, means for sliding said plates relative to each other along said first surfaces in a direction generally transverse to said axis, and engaging means for frictionally engaging and forcing a continuous cylindrical stock through said plates to create a pipette tip.

8. A dispensing station as defined in claim 7, wherein said engaging means comprise a pair of opposite, oppositely-rotating rollers.

9. A dispensing station as defined in claim 7, and further including a v-shaped support positioned to hold said probe in place within a horizontal plane when said probe is moved into a dispensing position.

* * * * *